(12) United States Patent
Weston et al.

(10) Patent No.: US 6,280,410 B1
(45) Date of Patent: Aug. 28, 2001

(54) METHOD OF FILLING A DRUG CAPSULE AND ARTICLE PRODUCED THEREBY

(75) Inventors: Terence Edward Weston, Eye; John Nicholas Walker, Frodsham Cheshire, both of (GB)

(73) Assignees: Weston Medical Limited, Suffolk; Medeva Europe Limited, London, both of (GB)

( * ) Notice: Subject to any disclaimer, the term of this patent is extended or adjusted under 35 U.S.C. 154(b) by 0 days.

(21) Appl. No.: 09/169,922

(22) Filed: Oct. 2, 1998

(30) Foreign Application Priority Data

Apr. 2, 1996 (GB) .................................. 9606904
Apr. 27, 1996 (GB) .................................. 9608782

(51) Int. Cl.[7] ........................................ A61M 5/30
(52) U.S. Cl. ............................... 604/72; 604/232
(58) Field of Search ............... 604/523, 68–72, 604/232; 141/2, 18, 19

(56) References Cited

U.S. PATENT DOCUMENTS

| | | | |
|---|---|---|---|
| 3,729,031 | 4/1973 | Baldwin | 141/2 |
| 3,945,383 * | 3/1976 | Bennett et al. | 128/272 |
| 4,010,747 | 3/1977 | Clark et al. | 128/173 H |
| 4,227,528 | 10/1980 | Wardlaw | 128/218 A |
| 4,338,980 * | 7/1982 | Schwebel et al. | 141/18 |
| 4,351,692 | 9/1982 | Ouellette . | |
| 4,507,113 | 3/1985 | Dunlap . | |
| 4,518,385 | 5/1985 | Lindmayer et al. . | |
| 4,568,346 | 2/1986 | van Dijk | 604/414 |
| 4,662,878 | 5/1987 | Lindmayer . | |
| 4,898,209 | 2/1990 | Zbed | 137/614.04 |
| 5,062,830 | 11/1991 | Dunlop | 604/68 |
| 5,188,615 | 2/1993 | Haber et al. | 604/203 |
| 5,256,142 | 10/1993 | Colavecchio | 604/68 |
| 5,503,627 * | 4/1996 | McKinnon et al. | 604/72 |
| 5,879,327 | 3/1999 | DeFarges et al. | 604/68 |
| 5,938,637 * | 8/1999 | Austin et al. | 604/72 |

FOREIGN PATENT DOCUMENTS

| | | |
|---|---|---|
| 0 201 638 | 11/1986 | (EP) . |
| 0 328 504 | 8/1989 | (EP) . |
| 0 412 621 | 2/1991 | (EP) . |
| 0 526 772 | 2/1993 | (EP) . |
| 0 737 484 | 10/1996 | (EP) . |
| 824357 | 2/1938 | (FR) . |
| 206 016 | 8/1990 | (HU) . |
| 133435 | 11/1966 | (NL) . |
| WO 95/03844 | 2/1995 | (WO) . |
| WO95/24176 | 9/1995 | (WO) . |
| WO96/15821 | 5/1996 | (WO) . |
| WO 96/28202 | 9/1996 | (WO) . |
| WO 97/22375 | 6/1997 | (WO) . |
| WO98/12121 | 3/1998 | (WO) . |

* cited by examiner

*Primary Examiner*—Richard K. Seidel
*Assistant Examiner*—Kevin C. Sirmons
(74) *Attorney, Agent, or Firm*—Darby & Darby

(57) ABSTRACT

A needleless injector drug capsule assembly comprising a container, housing therefor, a piston, and resilient seals to permit filling and sealing thereafter to maintain sterility of the contents.

17 Claims, 3 Drawing Sheets

METHOD OF FILLING A DRUG CAPSULE AND ARTICLE PRODUCED THEREBY

FIELD OF THE INVENTION

Background of the Invention

This invention relates to a method of filling a disposable drug capsule for assembly to a needleless injector, and to an article produced thereby.

Needleless injectors are used as an alternative to hypodermic syringes to inject drugs through a patient's skin into the underlying tissues. A typical injector comprises a high pressure pump which dispenses a dose of liquid drug through a small hole with sufficient force to pierce the epidermis and diffuse into the tissues. This technique has been in use for over fifty years, and there are many patents covering various constructional details. A feature of practically all prior art injectors is that they are filled with drug by the user before injection: this has resulted in a number of inconvenient preparatory steps and the need to sterilize the drug chamber between each operation.

There has been a marked trend over the past twenty years to supply liquid drugs and other liquids for medical use pre-packed—for example, the familiar prefilled hypodermic syringe, or intravenous infusion bags containing a saline solution. Such presentation has several advantages: the stringent requirements for sterility are met by the manufacturer; the dosage is correct; separate vials of drug and separate syringes are not required; distribution of small quantities is facilitated; convenience and ease of use result in significant cost savings.

Needleless injectors have generally not taken advantage of these trends, and this has been a factor in the lack of widespread use of such devices. Whilst there have been attempts to use prefilled capsules, these have largely failed to address the problems and techniques associated with aseptic filling and maintaining sterility after filling. Thus, what appeared to be promising advances in the art were frustrated by the inability to aseptically fill at an economical price, and such inventions rarely progressed from laboratory prototypes.

SUMMARY OF THE INVENTION

According to the present invention there is provided a method of filling a needleless injector capsule with a drug in a liquid form, and sealing the capsule after filling, the capsule defining a chamber which communicates with the exterior prior to sealing, via an orifice in the capsule wall and an orifice in an adjacent seal held in a seal carrier, the method comprising:

(a) introducing liquid into the chamber via the seal orifice and the capsule orifice, and (b) closing off the seal carrier to the exterior.

The invention further provides a filled and sealed drug-containing article, which comprises a needleless injector capsule defining a chamber having a drug in liquid form therein, the capsule having an orifice through a wall thereof, a seal carrier having therein a seal in which is formed an orifice communicating with the capsule orifice, and closing means for closing the seal carrier to the exterior whereby to seal off the drug in the chamber from the exterior.

A preferred embodiment comprises a hollow cylindrical capsule open at one end, and terminating in a fine hole which is the injection orifice to be placed upon the skin. A piston is slidingly and sealing located within the capsule bore adjacent to the orifice. The capsule is retained within a housing configured to connect to a needleless injector power source. Frangibly attached to the housing at the orifice end is a short tube which carries a resilient seal adapted to receive a filling needle. After filling, the filling needle is withdrawn, and a resilient plug is inserted into the short tube to form a sterile seal. During the filling process, the piston within the capsule is driven by the hydraulic pressure of the drug to some predetermined position with respect to the required fill volume. The filled capsule is then attached to the injector energy source. Before use, the frangibly connected tube is snapped off complete with the resilient seals, thus exposing the capsule orifice. The injector is then operated according to the required methodology.

BRIEF DESCRIPTION OF THE DRAWINGS

A detailed description follows, with reference to the accompanying drawings, all of which, except

FIG. 5a is an end view of what is shown in FIG. 5;

DETAILED DESCRIPTION OF THE INVENTION

Figure 1:
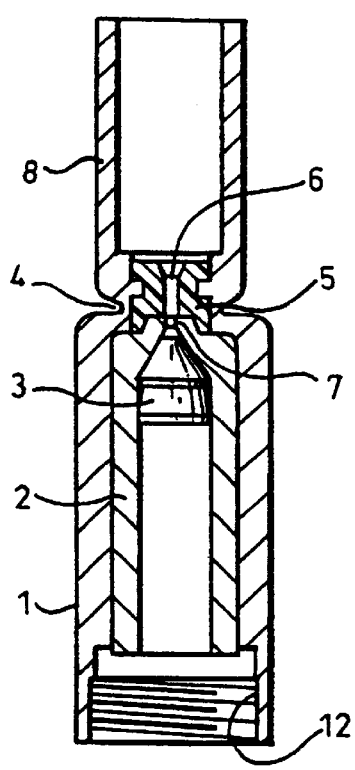
FIG. 1 shows the capsule, housing and seal carrier assembled and empty.

FIG. 1 shows a capsule 2 in the form of a hollow cylindrical chamber having a small injection orifice 7 at one end and containing a resilient piston 3 located adjacent to the orifice 7. As shown, the internal shape of the capsule 2 is preferably frusto-conical adjacent the orifice 7 to aid flow of the liquid during injection, and the piston is of a similar shape to reduce dead volume.

Figure 7:
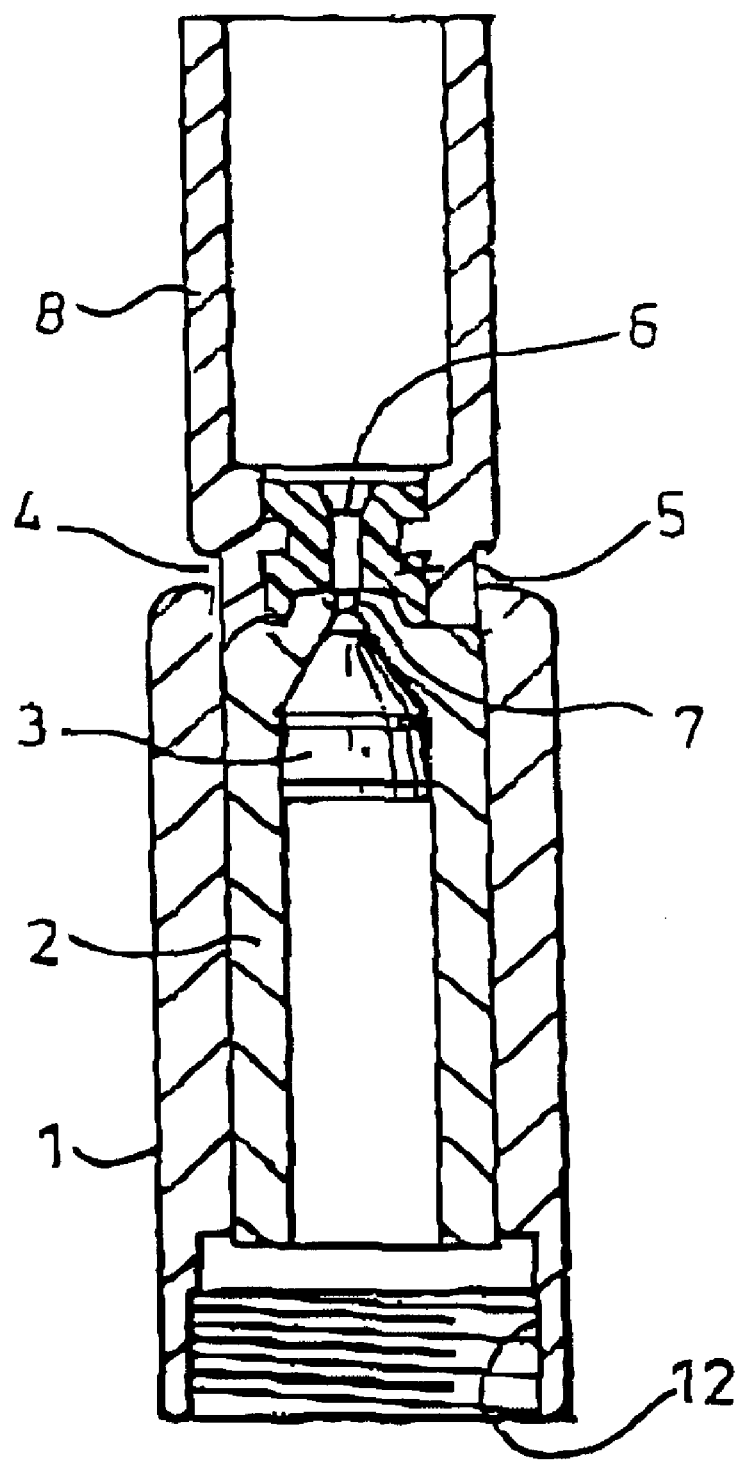
FIG. 7 shows an alternate embodiment of the capsule, housing and seal carrier assembled and empty, with the sealed carrier attached to the capsule.

The assembly of capsule 2 and piston 3 is retained within a housing 1, either by friction of by mechanical means. Housing 1 has a thread 12 or other means for attaching the assembly to a needleless injection power source. A seal carrier 8, in the form of a short tube, is frangibly attached by a frangible connection 4 to the housing 1, and contains a resilient seal 5. The seal carrier 8 may also be attached directly to capsule 2, as shown in FIG. 7. Alternatively, the seal carrier 8 may be attached to housing 1 by snap fitting or other mechanical means. The resilient seal 5 has an aperture 6 therethrough which is in hydraulic connection with the orifices 7 in capsule 2, and the cooperating faces of the capsule 2 and the seal 5 form an hydraulic seal.

Figure 2:
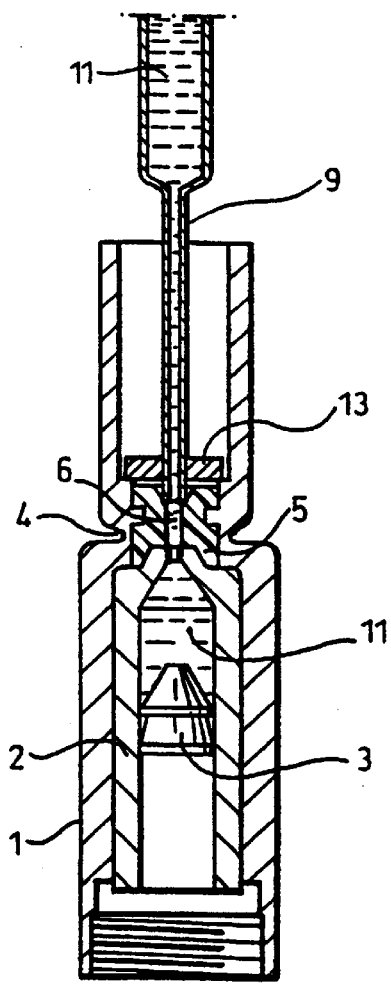
FIG. 2 shows the filling needle inserted.

Referring to FIG. 2, a filling needle 9 is inserted sealingly into the aperture 6 of seal 5, and injectate 11 is forced under pressure through the orifice 7 into the capsule 2. Hydraulic pressure forces the piston 3 along the bore of the capsule 2 to a predetermined position which represents the volume to be injected, after which the filling needle 9 is withdrawn. Filling needle 9 may have a stop 13 to control the depth of penetration of the filling needle 9 in the hole 6 of seal 5. Stop 13 may also be a locational sliding fit within the bore of the seal carrier 8 to assist in guiding the needle 9 into aperture 6.

Figure 3:
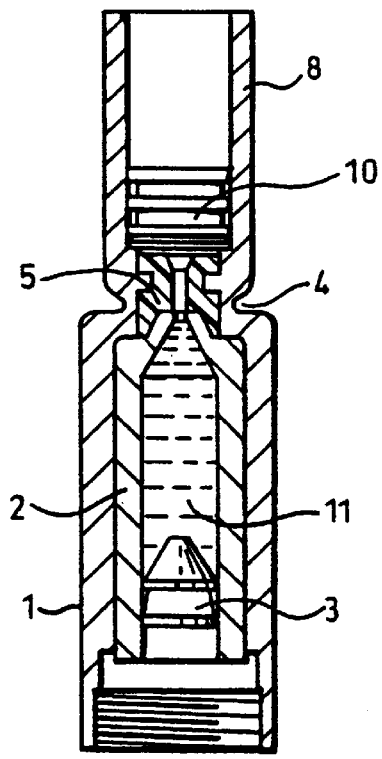
FIG. 3 shows the capsule filled and sealed.

After filling, a resilient plug 10 is inserted into the bore of the seal carrier 8, as shown in FIG. 3. Thus, the injectate 11 is sealed within the capsule by the resilient plug 10, the resilient piston 3, and the seal between the face of seal 5 and capsule 2.

Preferably all the components except resilient plug 10 are supplied to the filler in a sterile condition and pre-assembled, but of course they may be supplied separately and sterilised prior to filling. The filling is preferably conducted under sterile conditions, so that any air trapped within the injectate 11, or between seal 5 and plug 10, is sterile. Alternatively, the completely filled assembly may be sterilized after filling by heat or radiation if appropriate.

Figure 4:
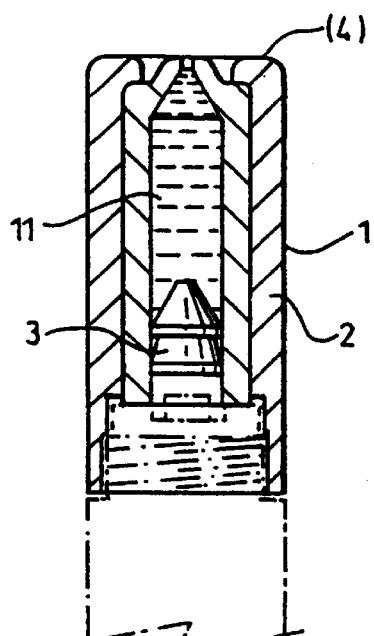
FIG. 4 depicts the capsule attached to an injector energy source, and prepared for use.

FIG. 4 shows the filled capsule and housing attached to a needleless injector power source, and prepared for use by snapping off the seal carrier 8 together with seal 5 and plug 10.

Figure 5A:
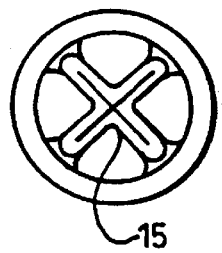
FIG. 5a, are centre-line sectioned drawings. In the drawings.
Figure 5:
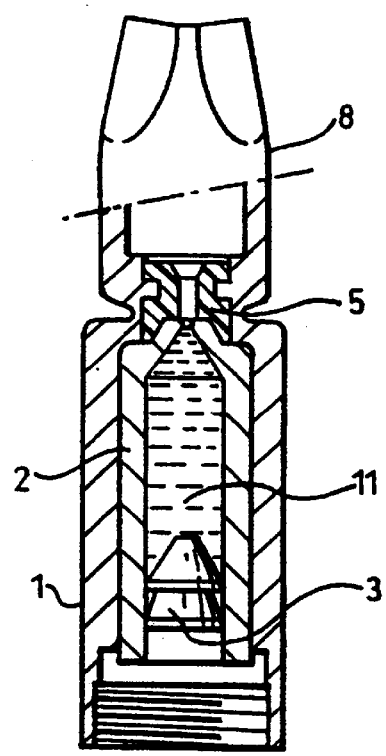
FIG. 5 shows a filled and sealed capsule, sealed by an alternative sealing method.

An alternative method of sealing the capsule after filling is shown in FIGS. 5 and 5*a*. Seal carrier 8 is manufactured in a material which may be deformed, by the action of heat for example, and crimped together to form a seal as shown diagrammatically at 15. The seal may be improved if the material is melted at the joint or coated with a suitable meltable sealant/adhesive. Other methods of effecting the seal include ultrasonic welding, friction welding, radiation-curing sealant, or a separate clamping component to hold the walls of seal carrier 8 in sealing contact. Thus the basic principle of sealing according to FIG. 5 is to deform the seal carrier 8 so that the inner walls make and maintain sealing contact.

Figure 6:
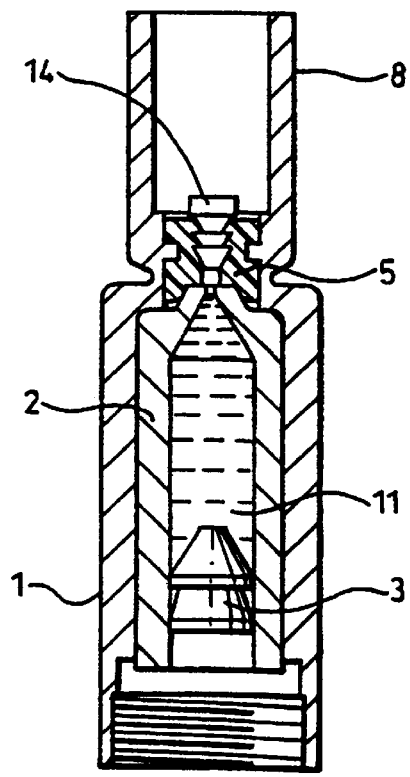
FIG. 6 shows a filled capsule sealed by another alternative sealing method.

Another alternative sealing method is shown in FIG. 6. Here, a plug 14 is sealingly inserted into the filling hole 6 of resilient seal 5 after filling.

The preferred material for the capsule is glass, and for the piston polytetrafluoroethylene (PTFE), but other combinations are suitable according to the intended application. Alternatively, the capsule may be made of the same material as the housing, and for convenience be manufactured as one component. The seal carrier is then directly attached to what is, in effect, the capsule itself. Yet another variation is for the housing to be moulded on to the capsule. In the case of a glass capsule, it is desirable to assemble it to, or mould it on, the housing soon after manufacture of the glass to prevent abrasive damage to the glass.

The procedures and components described permit a conventional syringe filling machine to be used with the minimum of modification. If small numbers of capsules are to be filled, then the filling needle 9 may be replaced by a conventional hypodermic syringe needle, and the drug may be dispensed from a syringe.

If it is required to reduce the volume of trapped air within the assembly, the air may be evacuated immediately prior to inserting the filling needle.

What is claimed is:

1. A filled and sealed drug-containing article for attachment to a needleless injector power source, which comprises a needleless injector capsule defining a chamber having a drug in liquid form therein, the capsule having an orifice through a wall thereof, a seal carrier having therein a seal in which is formed an orifice communication with the capsule orifice, the seal being in sealing contact with the capsule wall around the orifice in the capsule wall, and closing means for closing the seal carrier to the exterior whereby to seal off the drug in the chamber from the exterior, the capsule being retained in a housing and the seal carrier being removably attached to one of the housing and the capsule, and connecting means for connecting said article to a needleless injector power source wherein the closing means comprises a plug inserted in the seal carrier wherein the closing means comprises a plug inserted in the seal carrier.

2. An article according to claim 1, wherein the seal carrier is frangibly attached to the housing or capsule.

3. An article according to claim 1, wherein the housing is present and is molded onto the capsule.

4. An article according to claim 1, wherein the seal carrier is in the form of a tube.

5. An article according to claim 1, wherein a piston is received within the capsule chamber, the drug being between the piston and the capsule wall through which the capsule orifice extends.

6. An article according to claim 1, comprising an attachment element for enabling said attachment to a needleless injector power source.

7. An article according to claim 6, wherein said attachment element is in the form of a thread.

8. An article according to claim 1, wherein the seal carrier is integral with one out of the housing and the capsule.

9. A filled and sealed drug-containing article for attachment to a needleless injector power source, which comprises a needleless injector capsule defining a chamber having a drug in liquid form therein, the capsule having an orifice through a wall thereof, a seal carrier having a seal in which is formed an orifice communicating with the capsule orifice, the seal being in sealing contact with the capsule wall around the orifice in the capsule wall, and closing means for closing the seal carrier to the exterior whereby to seal off the drug in the chamber from the exterior, the capsule being retained in a housing and the seal carrier being removably attached to one of the housing or the capsule, and connecting means for connecting said article to a needleless injector power source, wherein the seal carrier is frangibly attached to the housing or capsule.

10. An article according to claim 9, wherein the closing means is a plug inserted in the seal orifice.

11. An article according to claim 9, wherein the closing means is provided by a deformed wall portion of the seal carrier.

12. An article according to claim 9, wherein the housing is present and is molded onto the capsule.

13. An article according to claim 9, wherein the seal carrier is in the form of a tube.

14. An article according to claim 9, wherein a piston is received within the capsule chamber, the drug being between the piston and the capsule wall through which the capsule orifice extends.

15. An article according to claim 9, comprising an attachment element for enabling said attachment to a needleless injector power source.

16. An article according to claim 15, wherein said attachment element is in the form of a thread.

17. An article according to claim 9, wherein the seal carrier is integral with one out of the housing of the capsule.

* * * * *

UNITED STATES PATENT AND TRADEMARK OFFICE
CERTIFICATE OF CORRECTION

PATENT NO. : 6,280,410 B1
DATED : August 28, 2001
INVENTOR(S) : Terence Edward Weston et al.

It is certified that error appears in the above-identified patent and that said Letters Patent is hereby corrected as shown below:

<u>Title page,</u>
Item [75], Inventors, change "Terence Edward Weston, Eye" to -- Terence Edward Weston, Eye, Suffolk (GB) --

Signed and Sealed this

Thirteenth Day of August, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,280,410 B1
DATED         : August 28, 2001
INVENTOR(S)   : Terence Edward Weston et al.

It is certified that error appears in the above-identified patent and that said Letters Patent is hereby corrected as shown below:

<u>Title page,</u>
Item [75], Inventors, change "Terence Edward Weston, Eye" to -- Terence Edward Weston, Eye, Sulfolk (GB) --

Signed and Sealed this

Fifteenth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,280,410 B1  Page 1 of 1
APPLICATION NO. : 09/169922
DATED : August 28, 2001
INVENTOR(S) : Weston et al.

It is certified that error appears in the above-identified patent and that said Letters Patent is hereby corrected as shown below:

Title page, add Item [63] Related U.S. Application Data:
Continuation of Application No. PCT/GB97/00889, Filed on March 27, 1997

Column 1, After the Title, add:
This is a Continuation of International Application PCT/GB97/00889, Filed March 27, 1997.

Col 3 line 61, change "communication" to --communicating--.

Signed and Sealed this

Third Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 6,280,410 B1 Page 1 of 1
APPLICATION NO. : 09/169922
DATED : August 28, 2001
INVENTOR(S) : Terence Edward Weston et al.

It is certified that error appears in the above-identified patent and that said Letters Patent is hereby corrected as shown below:

Please delete the phrase in claim 1 beginning in col. 4, line 8 as follows "wherein the closing means comprises a plug inserted in the seal carrier" as it is duplicative of the phrase in col. 4, lines 7-8.

Signed and Sealed this

Third Day of March, 2009

JOHN DOLL
*Acting Director of the United States Patent and Trademark Office*

UNITED STATES PATENT AND TRADEMARK OFFICE
CERTIFICATE OF CORRECTION

PATENT NO.        : 6,280,410 B1                                    Page 1 of 1
APPLICATION NO.   : 09/169922
DATED             : August 28, 2001
INVENTOR(S)       : Terence Edward Weston et al.

It is certified that error appears in the above-identified patent and that said Letters Patent is hereby corrected as shown below:

Please delete the phrase in claim 1 beginning in col. 4, line 7:

"wherein the closing means comprises a plug inserted in the seal carrier"

This phrase is a duplicate of the same phrase appearing at col. 4, lines 8-9.

Signed and Sealed this

Twenty-fourth Day of November, 2009

David J. Kappos
*Director of the United States Patent and Trademark Office*